United States Patent
Cull et al.

(10) Patent No.: US 8,246,579 B2
(45) Date of Patent: Aug. 21, 2012

(54) SURGICAL SYSTEM HAVING MEANS FOR PRESSURIZING VENTING VALVE

(75) Inventors: Laurence J. Cull, Wildwood, MO (US); Mark Ian Lutwyche, Reisterstown, MD (US)

(73) Assignee: Bausch & Lomb Incorporated, Rochester, NY (US)

( * ) Notice: Subject to any disclaimer, the term of this patent is extended or adjusted under 35 U.S.C. 154(b) by 706 days.

(21) Appl. No.: 11/961,293

(22) Filed: Dec. 20, 2007

(65) Prior Publication Data

US 2009/0163853 A1    Jun. 25, 2009

(51) Int. Cl.
A61M 1/00        (2006.01)
(52) U.S. Cl. ........ 604/118; 604/119; 604/120; 604/121; 604/30; 604/31; 604/35
(58) Field of Classification Search ............ 604/30, 604/118–121, 35, 31
See application file for complete search history.

(56) References Cited

U.S. PATENT DOCUMENTS

| | | | | |
|---|---|---|---|---|
| 3,812,855 | A * | 5/1974 | Banko | 604/31 |
| 3,902,495 | A | 9/1975 | Weiss et al. | 128/276 |
| 4,832,685 | A * | 5/1989 | Haines | 604/30 |
| 5,242,404 | A | 9/1993 | Conley et al. | 604/119 |
| 5,569,188 | A | 10/1996 | Mackool | 604/67 |
| 6,083,195 | A | 7/2000 | Perkins et al. | 604/30 |
| 6,224,583 | B1 | 5/2001 | Perkins et al. | 604/408 |
| 6,599,271 | B1 | 7/2003 | Easley | 604/119 |
| 6,780,166 | B2 * | 8/2004 | Kanda et al. | 604/31 |
| 6,908,451 | B2 * | 6/2005 | Brody et al. | 604/118 |
| 7,083,591 | B2 | 8/2006 | Cionni | 604/31 |
| 2005/0060995 | A1 | 3/2005 | MacLeod | |
| 2006/0135974 | A1 | 6/2006 | Perkins | 606/169 |
| 2007/0179438 | A1 | 8/2007 | Morgan | 604/67 |

FOREIGN PATENT DOCUMENTS

| | | |
|---|---|---|
| EP | 1 080 739 A | 3/2001 |
| WO | WO 89/03230 A | 4/1989 |
| WO | WO2006/119557 | 11/2006 |
| WO | WO 2008/060995 A | 5/2008 |

OTHER PUBLICATIONS

International Search Report (PCTISA/210) and Written Opinion (PCT/ISA/237) mailed on May 9, 2009, pp. 1-8.

* cited by examiner

*Primary Examiner* — Bhisma Mehta
*Assistant Examiner* — Edelmira Bosques
(74) *Attorney, Agent, or Firm* — Jeffrey B. Powers

(57) ABSTRACT

The present invention provides a surgical system 10 for aspiration of a biological material comprising a source of irrigation fluid 24, a collection cassette 30, a pump 40 for creating a vacuum in the collection cassette 30, a handpiece 50 applied to a surgical area for infusing irrigation fluid and for aspirating a biological material, conduits 60 and 62 connecting the handpiece to each of the source of irrigation fluid and the collection cassette and means 70 for isolating the pump from the handpiece to prevent creation of vacuum within the conduit 62 and the collection cassette 30 after receiving a stop signal.

1 Claim, 2 Drawing Sheets

SURGICAL SYSTEM HAVING MEANS FOR PRESSURIZING VENTING VALVE

FIELD

The present invention relates generally to a system useful for various surgical procedures. More specifically, it relates to a surgical system having means for assisting air venting or pressure regulation in an ophthalmic surgical procedure.

BACKGROUND

A cataract is an opacity that develops in the crystalline lens of the eye or in its envelope. One medical procedure to remove a cataract-affected lens is phacoemulsification (phaco) using ultrasonic sound to break up or emulsify the cataract. A phacoemulsification machine typically includes a handpiece with both irrigation and aspiration functions. A phaco handpiece aspirates in emulsified fluids and simultaneously replaces those aspirated fluids with balanced salt solution (BSS) to maintain a proper pressure of the anterior chamber of the patient's eye. Such a handpiece is connected to a pump generating negative pressure or vacuum to drive aspiration, by which debris from the eye flow through a tube to means for collection such as a cassette, a bag, or bottle.

A common and potentially dangerous occurrence in ophthalmic surgery is "post-occlusion surge." During ophthalmic surgery, particularly cataract surgery, as the lens is broken-up and emulsified, such as during phacoemulsification, irrigation fluid is constantly infused into the surgical site and the fluid and emulsified tissue are aspirated away from the surgical site through the phaco handpiece. On occasion bits of tissue are larger than the aspiration lumen in the phaco handpiece, which can result in a clogged phaco needle. As long as the aspiration conduit remains clogged, a negative pressure builds up throughout the aspiration system. Then, after the clog has been removed, the system can experience what is commonly referred to as surge. Post-occlusion surge can cause serious damage to a patient's eye, such as by rupturing a capsular bag and allowing vitreous to leak from the eye's posterior into the eye's anterior chamber or cause irreparable damage to the cornea's endothelial cells. Generally speaking, endothelial cells are not regenerated naturally and it is crucial to prevent post-occlusion surge in an ophthalmic operation.

Air evacuating pumps, such as a rotary vane pump and a venturi pump, are widely used as sources of vacuum for surgical aspiration. In the case of a rotary pump, for example, spinning of the rotor is necessary to force fluid to move through a tube to a reservoir where the spinning of the rotor generates vacuum to drive aspiration. One way to reduce post-occlusion surge is to sense an occlusion at the tip of the handpiece or the conduit and direct the pump to stop so that vacuum is not generated any more.

Another approach is to monitor and control the fluidic pressure automatically to reduce excessive negative pressure. For example, U.S. Pat. No. 3,902,495 describes a control system containing a relief valve discharging undue pressure from the tube upon reaching a predetermined pressure.

However, the methods mentioned above and other conventional pressure controlling methods failed to recognize or solve the problem that disconnection of an energy source, such as turning off the vacuum pump, or introducing a relief valve does not lead to an immediate stop because the pump has momentum to continue its motion. Such momentum continues to generate negative pressure notwithstanding the disconnection of the energy source of the pump, resulting in a delay in ceasing the generation at a negative pressure and the stop signal. Given that the anterior chamber is considerably small in volume, the delay in stopping the pump can cause damage to the eye. Therefore, there is a need to increase the efficiency of pressure equalizing in ophthalmic surgery.

SUMMARY OF THE INVENTION

It is therefore one of the objects of this invention to provide a surgical system that minimizes a generation of momentum-driven vacuum after receiving a stop signal so as to prevent post-occlusion surge efficiently during eye surgery.

In one embodiment, it is provided a surgical system comprising means for applying pressure to a venting valve to efficiently remove the undesirable effect of momentum-driven pumping after a stop signal.

In another embodiment, it is provided a surgical system for ophthalmic surgery comprising means applying pressure to a venting valve to efficiently remove the undesirable effect of momentum-driven pumping after a stop signal.

Yet in another embodiment, it is provided an ophthalmic surgical system for cataract surgery comprising means for applying pressure to a venting valve to efficiently remove the undesirable effect of momentum-driven pumping after a stop signal.

In another embodiment, it is provided a surgical system comprising means for applying pressure to a venting valve and a controller to monitor the intra-conduit pressure of the system and send a stop signal to the means for applying pressure.

In yet another embodiment, it is provided a surgical system for ophthalmic surgery comprising means for applying pressure to a venting valve and a controller to monitor the intra-conduit pressure of the system and send a stop signal to the means for applying pressure.

In another embodiment, it is provided a surgical system comprising means for applying pressure to a venting valve, one or more additional pressure relief valves to ease the pressure and a controller to monitor the intra-conduit pressure of the system and send a stop signal to the means for applying pressure and the additional pressure relief valves.

In another embodiment, it is provided a system for ophthalmic surgery comprising means for applying pressure to a venting valve, one or more additional pressure relief valves to ease the pressure and a controller to monitor the intra-conduit pressure of the system and send a stop signal to the means for applying pressure and the additional relief valves.

DETAILED DESCRIPTION

The following description is merely exemplary in nature and is not intended to limit the present disclosure, application, or uses.

Figure 1:
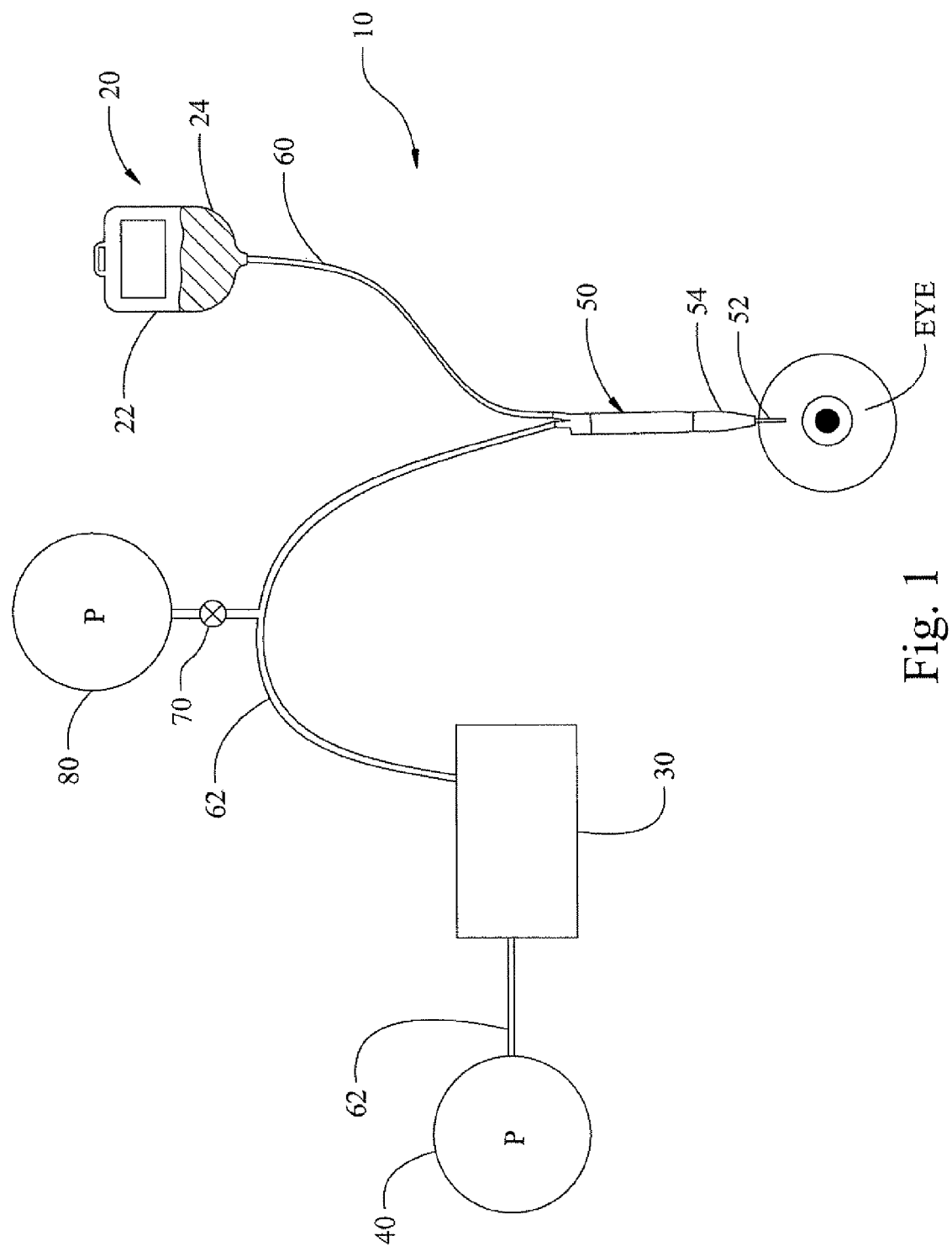
FIG. 1 is a diagrammatic view of one embodiment of a surgical system comprising means for applying pressure to a venting valve.

Referring to FIG. 1, the surgical system 10 comprises a source of irrigation fluid 20, a collection cassette 30, a vacuum pump 40, a surgical handpiece 50, conduits 60 and 62 connecting the surgical handpiece to each of the irrigation fluid source and the vacuum pump/the collection cassette, a venting valve 70 and means for applying pressure 80 to a valve 70. The surgical system 10 is particularly useful in ophthalmic surgery where it is necessary to break up and remove undesirable biological materials from the patient's eye. Specifically, the surgical system 10 can be used to remove cataract without causing irreparable damage to the eye.

The source of irrigation fluid 20 typically includes a fluid container 22 and surgical fluid 24. The surgical fluid can be any known surgical fluid and an ordinary skilled person in the art can select proper surgical fluid in accordance with the nature of the surgery to be operated. In an ophthalmic surgical system, the surgical fluid 24 is ophthalmic surgical fluid such as, for example, BSS. Each end of the conduit 60 is connected to the container 22 and the phaco handpiece 50 respectively so that the ophthalmic surgical fluid is delivered to the patient's eye through the irrigation sleeve 54 of the phaco handpiece 50.

The collection cassette 30 typically has a collection chamber and an inlet and an outlet for connection to each of the handpiece 50 and the vacuum pump 40. The collection chamber accommodates biological debris aspirated from the surgical site via the phaco needle 52 of the handpiece 50 and the aspiration conduit 62. The collection cassette 30 can be selected from any collection means for a surgical system known in the art, regardless of its reusability. Thus, the cassette 30 can be any known reusable or disposable collection means. For safety and sanity of the operation, it may be preferable to select a collection cassette equipped with a fluid level detection device which is designed to prevent overflowing and leaking surgical fluids. The collection cassette 30 is installed in operative association with the handpiece 50 and the pump 40 by any means known in the art.

The vacuum pump 40 is connected to the collection cassette 30 and the handpiece 50 through the aspiration conduit 62 to provide the aspiration system comprising the handpiece, the conduit and the collection cassette with negative pressure or vacuum. The vacuum pump 40 can be any pump known in the art as long as it is suitable for a surgical system including the present surgical system. Preferably, the vacuum pump 40 is one suitable for an ophthalmic surgical system. Examples of a pump applicable to the present invention are, but not limited to, a venturi pump, a rotary vane pump, a diaphragm pump, a liquid ring pump, a piston pump, a scroll pump, a screw pump, Wankel pump, an external vane pump, a booster pump, a multistage roots pump, a peristaltic pump, and a Toepler pump. Preferably, the pump is selected from a venturi pump, a rotary vane pump and diaphragm pump.

The surgical handpiece 50 can be a conventional phacoemulsification handpiece comprising a phaco needle 52 and an annular sleeve for irrigation 54 surrounding the needle. The surgical handpiece is placed on or into the surgical site to remove undesirable biological materials. In an ophthalmic surgical system, for example, the phaco handpiece 50 is inserted though an incision in an eye and the phaco needle coupled to an energy source applies energy, such as ultrasound and laser, to the surgical site to break up undesirable biological materials such as cataract. The surgical fluid 24 is infused into the surgical site through the annular sleeve 54 and the phaco needle 52 simultaneously aspirates fluids containing the undesirable materials away from the eye.

The surgical system 10 typically requires two separate conduits 60 and 62 for the irrigation and aspiration system. The irrigation conduit 60 connects the surgical handpiece 50 to the irrigation fluid source 20 to provide the surgical site with the surgical fluid 24, such as BSS. The irrigation system may contain one or more valves placeable between the handpiece 50 and the irrigation fluid source 20 to control the irrigation flow rate, thereby helping maintenance of a proper pressure of the surgical site.

The aspiration conduit 62 connects, for example, the surgical handpiece 50 to the collection cassette 30 and then to the vacuum pump 40, but it is obvious to an ordinary skilled person in the art that it is possible to modify the placement and the connection of the aspiration components. The vacuum pump 40 is operatively connected to the collection cassette 30 through the aspiration conduit 62 such that undesirable biological materials from the surgical site are aspirated to the collection cassette 30 for temporary storage and later disposal.

The venting valve 70 allows an air inflow into the aspiration conduit 62 to equalize the intra-conduit negative pressure. The venting valve 70 can be any valve known in the art suitable for controlling the intra-conduit pressure but which should be configured to be connectable to the means for applying pressure 80 to achieve the object of the present invention. It is obvious to an ordinary skilled person in the art that the venting valve 70 can be one or more and placeable anywhere in the aspiration system.

The means for applying pressure 80 to the venting valve 70 is connected to the valve 70 such that the pressure generated by the pressurizing means 80 forces atmospheric air into the valve 70. The means for applying pressure 80 infuses positive pressure into the valve 70 to equalize the negative pressure built up inside the aspiration conduit 62. It is obvious to an ordinary skilled person in the art that the pressurizing means 80 can be installed anywhere on the aspiration conduit 62. The pressurizing means 80 is designed to generate and apply positive pressure to the valve 70 immediately upon receiving a stop signal, resulting in accelerated venting. Accordingly, the means for applying pressure 80 can be a pump known in the art. There is no limitation in selecting a pump suitable for the present invention as long as it can produce positive pressure and be connectable to a venting valve. Preferably, the pressurizing means 80 is a pump suitable for a surgical system including the present surgical system. More preferably, the pressurizing means 80 is a pump tailored to an ophthalmic surgical system.

Figure 2:
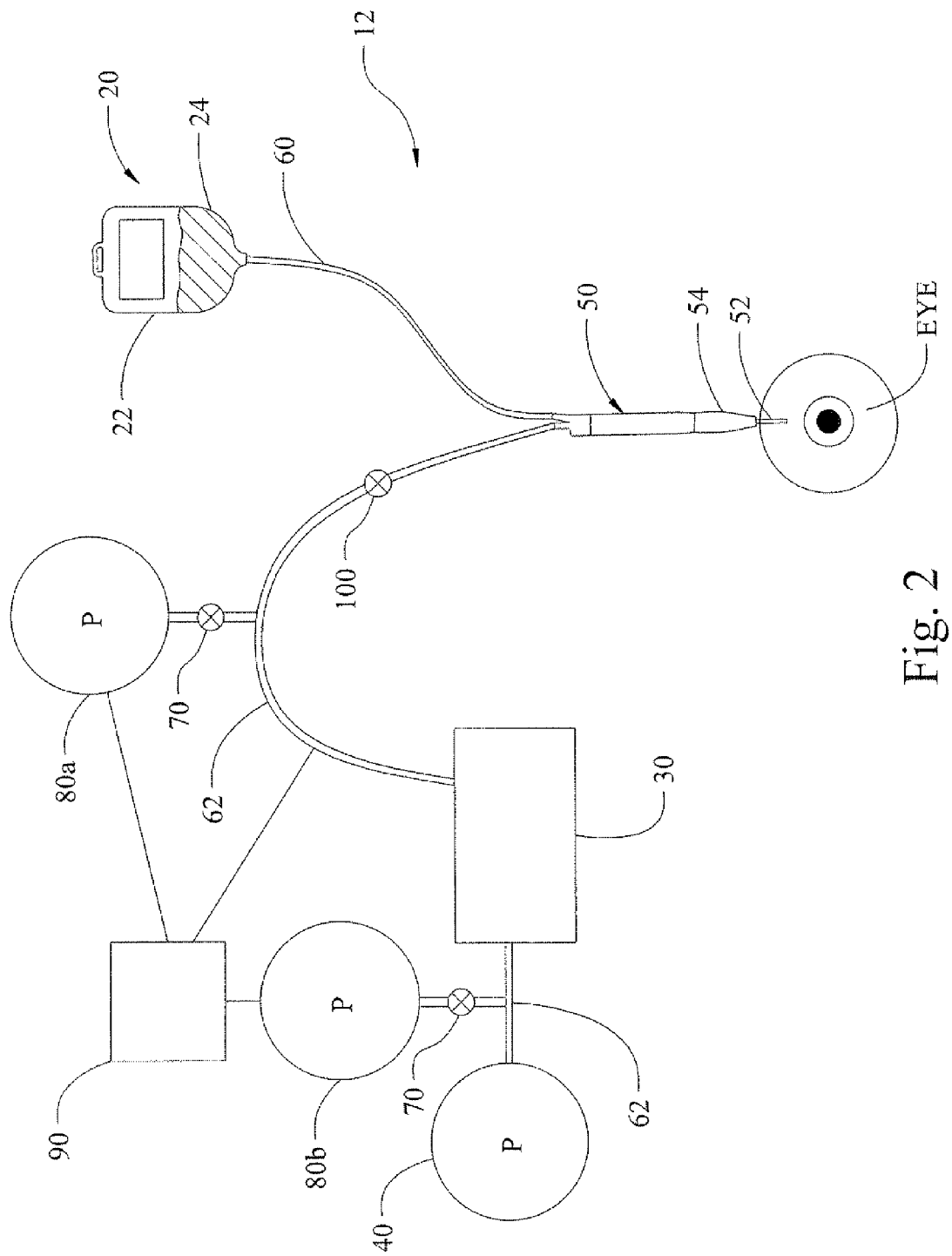
FIG. 2 is a diagrammatic view of another embodiment of a surgical system comprising means for applying pressure to a venting valve, a controller and an optional pressure relief valve.

Referring to FIG. 2, the surgical system 12 comprises, in addition to the components illustrated in FIG. 1, a controller 90 which is connected to the means 80 for applying pressure to the venting valve 70. The controller 90 is designed to send a stop signal to the means for applying pressure to the venting valve 70 when receiving a manual signal from an operator such as a surgeon or sensing a pre-determined level of pressure difference that can lead to post-occlusion surge. For automation of the isolation process, the controller 90 may contain means for monitoring the pressure of the aspiration conduit 62 and means for sending a mechanical or electronic signal to the means 80 for applying pressure to the venting valve 70. Therefore, in one embodiment, the controller 90 contains a pressure transducer capable of measuring the vacuum level of the aspiration conduit 62 and generating a signal to the means 80. The controller 90 can be computerized by electronic means to optimally control the surgical system based on various parameters where the electronic means determines the best timing for triggering the components to stop the aspiration system.

The surgical system 12 may have more than one pressurizing means 80a and 80b coupled to each of one or more venting valves to increase their efficiency of pressure equalization. For example, one pressurizing means 80a is installed between the cassette 30 and the handpiece 50, and the other 80b is between the pump 40 and the cassette 30 where each pressurized venting system removes negative pressure build-up within the aspiration conduit 62. The controller 90 may be linked to each of the pressurizing means to control the pressure equalization processes simultaneously.

The surgical system 12 optionally comprises a pressure relief valve 100 connected to the aspiration conduit 62 to prevent post-occlusion surge in the surgical site such as the eye chamber. The pressure relief valve 100 can be a vacuum level control valve allowing an air flow into the aspiration conduit 62 at a pre-determined pressure. The surgical system 12 may have one or more pressure relief valves 100 to maximize the efficiency of preventing post-occlusion surge. In one embodiment, the controller 90 is linked to each of the pressurizing means 80 and the pressure relief valve 100 so that the controller 90 controls both components simultaneously. A stop signal generated by the controller 90 directs these components to work in unison to prevent post-occlusion surge. In such a system, one signal results in prompt equalization of the negative pressure within the aspiration system.

The embodiments are described in order to best explain the principles of the invention and its practical application to thereby enable others skilled in the art to best utilize the invention in various embodiments and with various modifications.

As various modifications could be made in the constructions and methods herein described and illustrated without departing from the scope of the invention, it is intended that all matter contained in the foregoing description or shown in the accompanying drawings shall be interpreted as illustrative rather than limiting. Thus, the breadth and scope of the present invention should not be limited by any of the above-described exemplary embodiments, but should be defined only in accordance with the following claims and their equivalents.

What is claimed is:

1. A surgical system for aspiration of a biological material comprising: a source of irrigation fluid; a collection cassette; a vacuum pump for creating a vacuum in the collection cassette; a handpiece applied to a surgical area for infusing irrigation fluid and for aspirating a biological material; a conduit connecting the handpiece to each of the source of irrigation fluid and the collection cassette; a venting valve connected between the vacuum pump and the collection cassette; a pressure pump for applying positive pressure to the venting valve to equalize the an intra-conduit pressure, including the collection cassette vacuum, promptly after receiving a stop signal and a controller configured to send the stop signal to the venting valve.

* * * * *